United States Patent
Werner et al.

(10) Patent No.: US 9,841,366 B2
(45) Date of Patent: Dec. 12, 2017

(54) METHOD AND DEVICE FOR DETERMINING THE CONSUMPTION OF ELECTRODE MATERIAL DURING THE OPERATION OF AN ELECTRIC FURNACE

(71) Applicant: SGL CARBON SE, Wiesbaden (DE)

(72) Inventors: Franz-Xaver Werner, Meitingen (DE); Stefan Fischer, Meitingen (DE); Martin Christ, Meitingen (DE)

(73) Assignee: SGL Carbon SE, Wiesbaden (DE)

( * ) Notice: Subject to any disclaimer, the term of this patent is extended or adjusted under 35 U.S.C. 154(b) by 108 days.

(21) Appl. No.: 14/566,890

(22) Filed: Dec. 11, 2014

(65) Prior Publication Data

US 2015/0096811 A1   Apr. 9, 2015

Related U.S. Application Data

(63) Continuation of application No. PCT/EP2013/060519, filed on May 22, 2013.

(30) Foreign Application Priority Data

Jun. 11, 2012   (DE) .................... 10 2012 209 733

(51) Int. Cl.
   *G01N 5/00*   (2006.01)
   *C21C 5/52*   (2006.01)
   (Continued)

(52) U.S. Cl.
   CPC .............. *G01N 5/00* (2013.01); *B66C 13/16* (2013.01); *C21C 5/5211* (2013.01); *F27D 11/00* (2013.01);
   (Continued)

(58) Field of Classification Search
   CPC .......... G01G 19/16; G01G 19/18; G01G 3/13; G01G 19/14; C22B 9/00; C22B 9/18;
   (Continued)

(56) References Cited

U.S. PATENT DOCUMENTS 3,614,284 A * 10/1971 Scheidig ................ H05B 7/109
                                                    373/105
3,622,678 A    11/1971 Allen
                        (Continued)

FOREIGN PATENT DOCUMENTS

DE           1934218 B2    4/1977
EP           0647836 A1    4/1995
                        (Continued)

OTHER PUBLICATIONS

Computer Translation of JPH02-306137, Aug. 11, 2016.*
                        (Continued)

*Primary Examiner* — Randy Gibson
(74) *Attorney, Agent, or Firm* — Laurence A. Greenberg; Werner H. Stemer; Ralph E. Locher

(57) ABSTRACT

A method determines the consumption of electrode material during the operation of an electric furnace, particularly an arc furnace for producing steel. The method determines a weight of an electrode column, which is arranged in the electric furnace or is to be introduced into the electric furnace, using a weighing device. A device for determining the consumption of electrode material of an electric furnace, particularly an arc furnace for producing steel, is provided for performing the method. The device contains a weighing device for determining the weight of at least one electrode column which is arranged in the electric furnace or is to be introduced into the electric furnace, wherein the weighing device is integrated in an operating device of a system containing the electric furnace. Vibration conditions of the electrode column during operation of the electric furnace can also be determined with the method and with the device.

17 Claims, 2 Drawing Sheets

(51) Int. Cl.
  *F27D 11/10* (2006.01)
  *H05B 7/10* (2006.01)
  *B66C 13/16* (2006.01)
  *G01G 19/14* (2006.01)
  *F27D 19/00* (2006.01)
  *G01G 3/14* (2006.01)
  *F27D 11/00* (2006.01)

(52) U.S. Cl.
  CPC .............. *F27D 11/10* (2013.01); *F27D 19/00* (2013.01); *G01G 3/14* (2013.01); *H05B 7/10* (2013.01); *C21C 5/5229* (2013.01); *C21C 2005/5288* (2013.01); *G01G 19/14* (2013.01); *Y02P 10/216* (2015.11)

(58) Field of Classification Search
  CPC ........... C22B 9/20; G01N 5/00; C21C 5/5211; C21C 5/5229; C21C 2005/5288; F27D 19/00; F27D 11/00; F27D 11/10; H05B 7/10; B66C 13/16; Y02P 10/216
  See application file for complete search history.

(56) References Cited

U.S. PATENT DOCUMENTS

| | | | | |
|---|---|---|---|---|
| 3,745,502 | A * | 7/1973 | Watanabe | G01L 1/2287 338/3 |
| 3,822,111 | A * | 7/1974 | Suzuki | C30B 15/28 117/202 |
| 4,091,229 | A * | 5/1978 | Wooding | C22B 9/18 373/42 |
| 4,303,797 | A * | 12/1981 | Roberts | H05B 3/00 373/52 |
| 4,569,056 | A * | 2/1986 | Veil, Jr. | H05B 7/07 373/49 |
| 4,621,331 | A * | 11/1986 | Iwata | B25J 13/083 294/907 |
| 4,742,528 | A * | 5/1988 | Stenzel | C22B 9/18 373/105 |
| 5,274,662 | A * | 12/1993 | Krepel | F27B 3/085 373/100 |
| 6,310,454 | B1 * | 10/2001 | Moran | G05B 13/027 177/25.13 |
| 6,330,270 | B1 | 12/2001 | Brustad et al. | |
| 6,481,298 | B1 * | 11/2002 | Stevens | G01L 5/28 73/121 |
| 2009/0010299 | A1* | 1/2009 | Kummer | F27B 3/085 373/69 |
| 2016/0097594 | A1* | 4/2016 | Popov | C22B 9/20 266/99 |
| 2016/0113073 | A1* | 4/2016 | Popov | C22B 9/20 164/514 |

FOREIGN PATENT DOCUMENTS

| | | |
|---|---|---|
| JP | H01230983 A | 9/1989 |
| JP | H02306137 A | 12/1990 |
| JP | H09229571 A | 9/1997 |
| JP | 2001124478 A | 5/2001 |
| WO | 9950625 A2 | 10/1999 |

OTHER PUBLICATIONS

Computer Translation of JP2001-124478, Aug. 11, 2016.*
Computer Translation of JPH01-230983, Aug. 11, 2016.*
Computer Translation of JPH09-229571, Aug. 11, 2016.*
Translation of JP h02-306137 (Daido Steel), Aug. 2, 2017.*

* cited by examiner

METHOD AND DEVICE FOR DETERMINING THE CONSUMPTION OF ELECTRODE MATERIAL DURING THE OPERATION OF AN ELECTRIC FURNACE

CROSS-REFERENCE TO RELATED APPLICATION

This is a continuation application, under 35 U.S.C. §120, of copending international application No. PCT/EP2013/060519, filed May 22, 2013, which designated the United States; this application also claims the priority, under 35 U.S.C. §119, of German patent application No. DE 10 2012 209 733.3, filed Jun. 11, 2012; the prior applications are herewith incorporated by reference in their entireties.

BACKGROUND OF THE INVENTION

Field of the Invention

The present invention relates to a method and device for determining the consumption of electrode material during the operation of an electric furnace and particularly during the operation of an arc furnace for producing steel.

Electric furnaces and particularly arc furnaces are used among other things for heating and melting input material, which can in particular contain steel or other metals and various additives. In the process, arc furnaces can be used in particular to produce and recover steel and other metals by melting down waste material, in particular scrap metal, such as steel scrap, for example.

In an arc furnace, an electrical voltage is applied between at least one electrode column and the input material located inside the arc furnace, which input material is in electrical contact with a bottom electrode of the arc furnace. As a result of the electrical voltage that is applied, an arc is struck between the tip of the electrode column facing the input material and the input material, the thermal energy generated by the arc being transferred to the input material, in particular by thermal radiation and thermal conduction. In this way the input material can be heated to temperatures above its melting point, for example to temperatures in the range of approximately 1800° C. and thus melted. In order to remove the extracted charge from the arc furnace, a tapping process is performed, following which a new charging or loading of the electric furnace with input material takes place.

An electrode column is typically composed of a plurality of electrodes made from a graphite-containing material, which are connected to one another via connecting pieces, referred to as threaded nipples, which are arranged at the ends of the electrodes and screwed into corresponding indentations in the electrode ends. During the operation of the arc furnace the electrodes, on which the arc is struck, are subjected to extreme electrical and thermal loads, which is why they are subject, particularly on their lower end facing the input material, to considerable wear and burn-off. For this reason, single electrodes are not normally used in such furnaces but rather electrode columns, which are fixed to a support arm and are displaced gradually downwards in the furnace during operation of the furnace in order to compensate for the shortening of the electrode column due to electrode wear and thus to keep the distance between the lower end of the electrode column and the surface of the input material constant. An electrode column is consequently understood to be not just an electrode column composed of a plurality of electrodes, but also an electrode column which has already been used up or burnt off to the extent that it now only contains one partially used up or burnt off electrode. By using such electrode columns, the furnace can be operated without interruption for longer than when single electrodes are used. When the length of the electrode column falls short of a certain minimum, one or more new electrodes are screwed to its upper end manually or preferably mechanically. These can either be screwed onto the electrode column that is located inside the furnace or alternatively, the electrode column can be removed from the furnace beforehand using a transport apparatus and, after one or more electrodes have been screwed on, re-introduced into the furnace.

The consumption of electrode material and consequently of electrodes in the electric furnace contributes to the operating costs of the electric furnace to a not inconsiderable degree and can, for example, make up about 5% of the operating costs. Accordingly, the specific consumption of electrode material in relation to the amount of charge extracted, i.e. the ratio of consumed electrode material to recovered steel for example, constitutes an important operating variable. In the process, the specific consumption of electrode material depends on different influencing variables, such as the electrode material used, the electrical operating current and the composition and quality of the input material, for example.

In order to estimate the effect of various operating modes of the electric furnace, for example, and/or various operating parameters of the melting process on the specific consumption of electrode material of the electric furnace and thus to be able to optimize the operation of the electric furnace, it is necessary to determine the consumption of electrode material of the electric furnace. In the process, it is particularly advantageous to determine the electrode material consumption for various operating intervals of the electric furnace separately in order to be able to analyze in a differentiated manner the specific electrode consumption depending on the various operating conditions prevailing during the individual operating intervals.

For this purpose, determining the number of electrodes taken from a storage facility and added to the electrode column during a certain period of time, for example one month, and using this to calculate the abovementioned ratio of consumed electrode material to recovered steel is known. No sufficiently accurate data can be determined in this way, however, for shorter periods of time, such as a few weeks or even one week, a few days or hours and in particular for a period between two consecutive tapping processes since no account is taken of the quantity of electrode material still contained in the electrode column at the respective beginning and end of the time interval being observed.

Furthermore, camera systems can be used for this purpose to take a photograph of the electrode column before and after an operating interval of the electric furnace respectively in order to measure burn-off rates of the electrode column occurring during the operating interval and from this to estimate the consumption of electrode material during the operating interval. However, a considerable outlay in terms of materials and personnel is necessary in order to take these photographs and analyze them accordingly. Moreover, the photographs can only be taken when the lid of the electric furnace is open and thus only at certain points in time during the operation of the electric furnace, and therefore this method is limited with regard to its flexibility in relation to the possible time intervals of the measurement of consumption. Furthermore, no sufficiently precise estimation of electrode consumption is obtained using this method either.

SUMMARY OF THE INVENTION

The object of the present invention is therefore to provide a method and a device which facilitate precise and reliable determination of the consumption of electrode material during the operation of an electric furnace during any desired time interval, in particular short operating intervals, such as between one tapping process and the next and moreover with a low outlay in terms of materials and particularly low outlay in terms of personnel.

According to the invention, the object is achieved by a method for determining the consumption of electrode material during the operation of an electric furnace, particularly an arc furnace for producing steel. The method includes determining the weight of at least one electrode column, which is arranged inside the electric furnace or is to be introduced into the electric furnace, by using a weighing device.

By determining, according to the invention, the weight of an electrode column, which is arranged inside the electric furnace or is to be introduced into the electric furnace, using a weighing device, the exact value of the amount of electrode material being used at that point in time in the electric furnace is determined reliably and directly. In particular, if this determination is carried out at at least two different points in time, how much electrode material was inside the electric furnace at the beginning and end of the time interval defined by these points in time is also calculated directly. Using the difference between the two weight values calculated in this manner, the exact value of the electrode material consumed in the relevant time interval, for example between two consecutive tapping processes of the electric furnace, can be determined. In this way simple, precise and reliable determination of the consumption of electrode material during any operating interval, which can be selected to be as short as required, of the electric furnace is possible.

In order to minimize the outlay in terms of time and personnel needed to determine the consumption of electrode material and to avoid it altogether if possible, the weight of the at least one electrode column is preferably determined automatically in the method according to the invention. For example, the weighing device can be controlled by an automatic control system in order to determine a measured value for the weight of the electrode column at predefined times.

In order to determine the consumption of electrode material occurring during a certain time or operating interval of the electric furnace, a development of the inventive idea proposes determining the weight of the at least one electrode column at at least two different points in time. The consumption of electrode material during the time interval determined by the two points in time can then be determined by establishing the difference between the two weight values. In particular, the weight of the at least one electrode column can be determined immediately before and after a continuous melt operation interval of the electric furnace, i.e. before and after a continuous time interval during which the electrode column is energized without interruption in order to heat up and melt the input material of the electric furnace. The electrode column weight can, of course, likewise be determined before and after a longer time interval, which includes a plurality of melt operation intervals of the electric furnace carried out at separate times from one another.

Since the method can particularly advantageously serve to analyze the influence of various operating conditions on the electrode material consumption, the consumption of electrode material is preferably determined for various melt operation intervals, various operating conditions being present during the individual melt operation intervals, such as various current densities being set or various types of steel being used. The consumption values are determined for each interval by determining and establishing differences between the electrode column weights immediately before and after the respective melt operation interval.

For example, the electrode column weight can be determined immediately before and after a tap-to-tap interval of the electric furnace, i.e. immediately before and after a time interval of the melt operation that directly follows a tapping of the electric furnace and that extends until the next tapping of the electric furnace.

During the operation of the electric furnace, new electrodes are normally added to the electrode column at regular intervals and connected thereto, in particular screwed thereto, in order to compensate for the consumption of electrode material caused by the burn-off of the electrode column during the operation of the furnace. The adding of new electrodes preferably takes place between two consecutive melt operation intervals of the electric furnace and consequently on a non-energized electrode column. In the event of adding an electrode to the electrode column, the weight of the electrode column can be determined immediately before adding the new electrode, in particular in order to be able to thus determine the consumption of electrode material during the melt operation interval carried out before adding the electrode. Alternatively, or preferably in addition to this, the weight of the electrode column can be determined immediately after adding the new electrode, namely in particular as a starting value for the calculation of the consumption of electrode material during the melt operation interval which follows the adding of the electrode. Preferably both of the above weights are determined. Equally, just the weight of the electrode column immediately before adding the new electrode can be determined and the weight of the electrode column immediately after adding the new electrode can be calculated therefrom by adding the weight of the added electrode.

If the exact weight of an electrode to be added to the electrode column is known, the known weight of the electrode to be added can also be used to calibrate the weighing device. For this purpose, the weight of the electrode to be added can, for example, be measured using the weighing device and the measured weight can be compared to the known actual weight of the electrode to be added and the weighing device thus calibrated depending on the result of the comparison. The measurement of the weight of the electrode to be added is preferably carried out either while the electrode is being transported to the electrode column in order to be added to the electrode column or immediately before the electrode is added to the electrode column. Furthermore, according to an advantageous embodiment of the present invention, it can be provided for a measurement of the weight of the electrode which is to be added or has been added, and a corresponding calibration of the weighing device to be carried out every time a new electrode is added to the electrode column.

According to another preferred embodiment of the present invention, it is preferable to automatically log the weight of the electrode column, which has been determined as described above, namely using an appropriate electronic storage device, for example. In this way, a comprehensive database of various analyses relating to the consumption of electrode material of the electric furnace can be created.

Moreover, within the scope of the present invention it is preferable to also detect the quantity of the charge extracted in the electric furnace at the time being observed or during the time interval or intervals being observed in order to be able to determine the specific consumption of electrode material of the electric furnace from the quotient of the consumption of electrode material and the extracted charge.

In the method according to the invention, the determination of the weight is preferably carried out by a weighing device integrated in an operating device of a system comprising an electric furnace. Integrated in this connection means that at least one component and preferably all components of the weighing device forms or form a structural and/or functional unit with at least one element of the operating device.

According to another advantageous embodiment of the present invention, the at least one weighing device for determining the weight of the at least one electrode column is integrated in a transport device, by which the electrode column, which is arranged in the electric furnace and is preferably held in the electric furnace by a holding device, is received and transported in the electric furnace and/or transported out of the electric furnace, and/or by which an electrode column arranged outside the electric furnace is transported into the electric furnace. The holding device is, for example, a holding device, by which the electrode column is held in position inside the electric furnace during the melt operation of the electric furnace and is gradually displaced downwards depending on the degree of the electrode burn-off in order to compensate for the shortening of the electrode column occurring as a result of the electrode burn-off and thus to keep the distance between the lower end of the electrode column and the surface of the input material constant. The weight of the electrode column can be determined in this embodiment without having to completely remove the electrode column from the electric furnace and/or from the holding device. For example, the transport device can be used to raise and/or lower the electrode column relative to the electric furnace and relative to the holding device between two melt operation intervals, for example in order to adjust the distance of the electrode column from the input material of the furnace, in particular after a new electrode has been added to the electrode column. In order to be able to receive the electrode column, the transport apparatus preferably has a coupling apparatus for coupling with the electrode column. Furthermore, the holding device can contain an adjusting device with which the position and in particular the height of the holding device and in particular also of an electrode column held by the holding device can be adjusted. For this purpose, the adjusting device can contain a hydraulic system, for example. In this embodiment the weighing device can be integrated in such an adjusting device of the holding device.

In the process, the transport device can also be used in particular for adding a new electrode to the electrode column and for connecting the electrode thereto. In the process, the electrode to be added can be transported by the transport device from a storage position to a position directly vertical above the electrode column that might be held by the holding device, it being possible for the transport device to have a positioning unit such as a laser unit, with which the precise mutual alignment and/or positioning of the new electrode and electrode column can be checked. The electrode, which has been brought into the correct position, can for example be connected to the electrode column by screwing a nipple provided in the electrode. After one or more new electrodes have been added to the electrode column, the electrode column can be released from the holding device and lowered a little way towards the electric furnace by the transport device in order to achieve the required distance between the tip of the electrode column and the input material of the electric furnace before the electrode column is fixed again by the holding device and held in position. Alternatively, the transport device can also move the electrode column from the holding device to another position in the electric furnace or outside of the electric furnace in order to fasten one or more new electrodes to the electrode column at that point before the thus completed electrode column is guided back to the holding device, fixed there and held in position.

The transport device is, for example, a crane device which contains a trolley, for example, which is preferably moved on a crane track, which is preferably horizontal and preferably extends vertically above the electric furnace and/or the holding device. As a coupling apparatus, the crane device can, for example, contain a crane hook arranged on a cable of the crane device, on which crane hook the electrode column can be hung. In this embodiment, the weighing device can, for example, contain crane scales hanging between the crane hook and the crane track.

According to a further advantageous embodiment of the present invention, the weighing device is integrated in a holding device by which the electrode column is held during the melt operation of the electric furnace. Since the electrode column is typically held by the holding device during the majority of the operating time of the electric furnace, the weighing device integrated in the holding device provides the possibility of determining the weight of the electrode column at almost any point in time and consequently at least almost continuously without having to modify the operating procedure of the electric furnace in order to do this and without additional electrode column movements having to be carried out. In particular in this embodiment, the weighing device can also be configured and used to detect, measure, and optionally record, vibrations occurring during the melt operation of the electric furnace, which can occur in particular in the electrode column as a result of the generation of the arcs by the electrode column, such that the weighing device fulfils a double function.

In order to detect the vibration condition, the weight of the electrode column during the operation of the electric furnace can be determined by the weighing device, for example. During the operation of the electric furnace, forces in addition to the weight force impact on the electrode column as a result of the arc being struck, for example, and can bring about a vibration movement of the electrode column. For this purpose, the weight of the electrode column during the operation of the electric furnace is preferably determined continuously by the weighing device or at least quasi-continuously, for example with a temporal resolution of from 1 to 500 Hz. By analyzing the values determined by the weighing device during the operation of the electric furnace, such a vibration condition of the electrode column can be detected, it also being possible in this embodiment in particular to determine the frequency and/or amplitude of the vibration. In particular, accelerations or vibration frequencies which are dangerous to the electrodes can thus be detected and the control of the furnace and/or hanging of the electrodes can be adjusted depending on this detection, it being possible to carry out an automatic emergency cut-out in particular before a critical state occurs. Moreover, the detection and measurement of the vibration condition of the electrode column can, for example, also be used to assess the operating condition of the electric furnace. For example, by detecting the vibration condition, scrap cave-ins can be detected, uncontrolled flashovers or arcs from the electrode column onto the wall of the electric oven can be detected or the risk of electrode breakages can be foreseen and electrode breakages can be prevented. According to a further embodiment, it can be provided for the height of the foamy slag of the electric furnace to be derived from the detected vibration condition of the electrode column. The information detected as described above can also be used to adjust and optimize the operation of the electric furnace. In particular, significantly reduced heat dissipation and thus more efficient operation of the electric furnace can be achieved and/or reduced vibration of the electrode column and a smoother mode of operation of the electric furnace can be achieved.

A holding device as described above for the electrode column can contain a support arm, which extends in a horizontal direction above the furnace and has a receptacle or clamp for the electrode column on its end on the furnace side. This clamp can have at least two clamping jaws opposite one another by which the electrode column can be clamped to the support arm. Starting from the support arm, the electrode column preferably extends through an opening in the furnace lid in a vertical direction into the electric furnace. In addition, the holding device can contain a substantially vertical pillar, on the upper end of which the support arm is attached. The holding device can be constructed so as to be height adjustable in a vertical direction in order to be able to adjust the height of the electrode column such that a desired distance between the tip of the electrode column and the input material of the electric furnace is maintained despite the varying length of the electrode column due to the burn-off of the electrode column. Apart from this, the holding device and in particular a support arm of the holding device preferably serves to supply the electrode column with power during the melt operation of the electric furnace and for this purpose it is preferably connected to an electrical power source via cables.

As a development of the inventive idea, it is proposed for the weight of the electrode column to be determined using at least one element, which is preferably a strain gauge, force transducer and/or pressure measuring element arranged inside a hydraulic system for adjusting the holding device for the electrode column. In the process, the at least one strain gauge can, for example, be a metallic strain gauge or an optical strain gauge and/or the at least one force transducer can be a load cell. A strain gauge arranged on a support arm of a holding device for the electrode column measures the strain or tensile stress generated in the support arm by the weight of the electrode column from which the weight of the electrode column can be determined. In principle, the strain gauge can also be arranged on a preferably vertical pillar of the holding device which supports the support arm or between the pillar and the support arm. Preferably, however, the strain gauge is attached in the region of the greatest strain of the support arm, namely on the upper side of the support arm near the pillar supporting the support arm in particular and/or approximately at the center of the support arm when viewed in the width direction of the support arm, it also being possible, however, to arrange the strain gauge outside of this centre. Moreover, a hydraulic system referred to above can be constructed in order to adjust the position of the holding device and an electrode column received in the holding device, namely with regard to height in particular. A pressure measuring element, which is arranged in the hydraulic system and measures the pressure of the hydraulic fluid of the hydraulic system, is particularly suitable for determining the weight of an electrode column held by the holding device. In principle, the weighing device can be integrated in any desired adjustment device of the holding device that is configured to carry out an adjustment as described above.

A force transducer, in particular a load cell, is likewise suitable for determining the weight of the electrode column and can, for example, be attached to the support arm and/or pillar of the holding device, the load cell preferably being connected to both the support arm and the pillar of the holding device such that it can perform measurements effectively. In principle, the weighing device can also comprise a plurality of strain gauges and/or a plurality of force transducers, it being possible for the plurality of strain gauges and/or force transducers to either carry out measurements, which are independent of one another, of the weight and strain or to be appropriately connected to one another in order to generate a common measured value.

A further advantage of the above embodiment is that a strain gauge and a force transducer can also each be suitable for detecting, measuring and optionally, recording vibrations occurring in the electrode column or associated components during the operation of the electric furnace.

A calibration of the weighing device is preferably carried out before the determination of the weight of the electrode column.

According to an advantageous embodiment, the weight of the electrode column is determined at a point in time at which the electrode column is not energized. Since no vibrations generated by arcs occur in the electrode column at this point in time, a particularly accurate measurement of the weight of the electrode column is possible in this way.

Within the scope of the present invention, the weight of the electrode column is preferably determined while at least a portion of the electrode column is in the electric furnace and/or is held by a holding device for the electrode column. Removing the electrode column from the electric furnace and/or the holding device especially for the purpose of determining the weight can thus be dispensed with, whereby spending additional time on determining the consumption of electrode material can be avoided.

The invention also relates to a device to determine the consumption of electrode material of an electric furnace, in particular an arc furnace for producing steel, the device containing at least one weighing device to determine the weight of at least one electrode column arranged in the electric furnace or to be introduced into the electric furnace, the weighing device being integrated in an operating device of a system containing an electric furnace. Such a device can be achieved at low cost and is particularly suitable for carrying out the method according to the invention described above. The advantages and advantageous embodiments described above in relation to the method for determining the consumption of electrode material apply accordingly to the device for determining the consumption of electrode material.

According to an advantageous embodiment of the invention, the device is configured in order to determine weight of the electrode column automatically. For this purpose, the device can, for example, comprise an electronic control which automatically controls the weighing device in order to determine the weight of the electrode column and generate a corresponding measured value, which is optionally recorded.

Furthermore, it is preferable for the device to comprise an electronic storage device and to be configured to record the weight of the electrode column automatically in the electronic storage device in order to thus facilitate a comprehensive evaluation and analysis of the data relating to the electrode material consumption.

According to a further preferred embodiment of the present invention, the weighing device is integrated in a transport device, which is configured to receive the electrode column, which is arranged in the electric furnace and is preferably held in the electric furnace by a holding device, and to transport it in the electric furnace and/or out of the electric furnace and/or to transport an electrode column located outside of the electric furnace into the electric furnace. As described in more detail above in relation to the method according to the invention, the transport device preferably contains a crane device, it being possible for the weighing device to have crane scales attached to the crane device.

According to a further advantageous embodiment of the present invention, the weighing device is integrated in a holding device, which is constructed to hold the electrode column during the melt operation of the electric furnace. The weighing device is preferably integrated in a support arm of the holding device, as described above in relation to the method according to the invention. Moreover, the weighing device can also be integrated in an adjusting device described above in relation to the method, in particular in a hydraulic system, in order to adjust the holding device.

The weighing device preferably contains at least one element, which is preferably a strain gauge, force transducer and/or pressure measuring element arranged in a hydraulic system for adjusting the holding device for the electrode column. In the process, the at least one strain gauge can, for example, be a metallic strain gauge, or an optical strain gauge and/or the at least one force transducer can be a load cell.

Moreover, it is preferable for the weighing device of the device to be constructed such that it determines the weight of the at least one electrode column continuously or at least quasi-continuously, preferably with a temporal resolution of from 1 to 500 Hz.

Other features which are considered as characteristic for the invention are set forth in the appended claims.

Although the invention is illustrated and described herein as embodied in a method and a device for determining the consumption of electrode material during the operation of an electric furnace, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
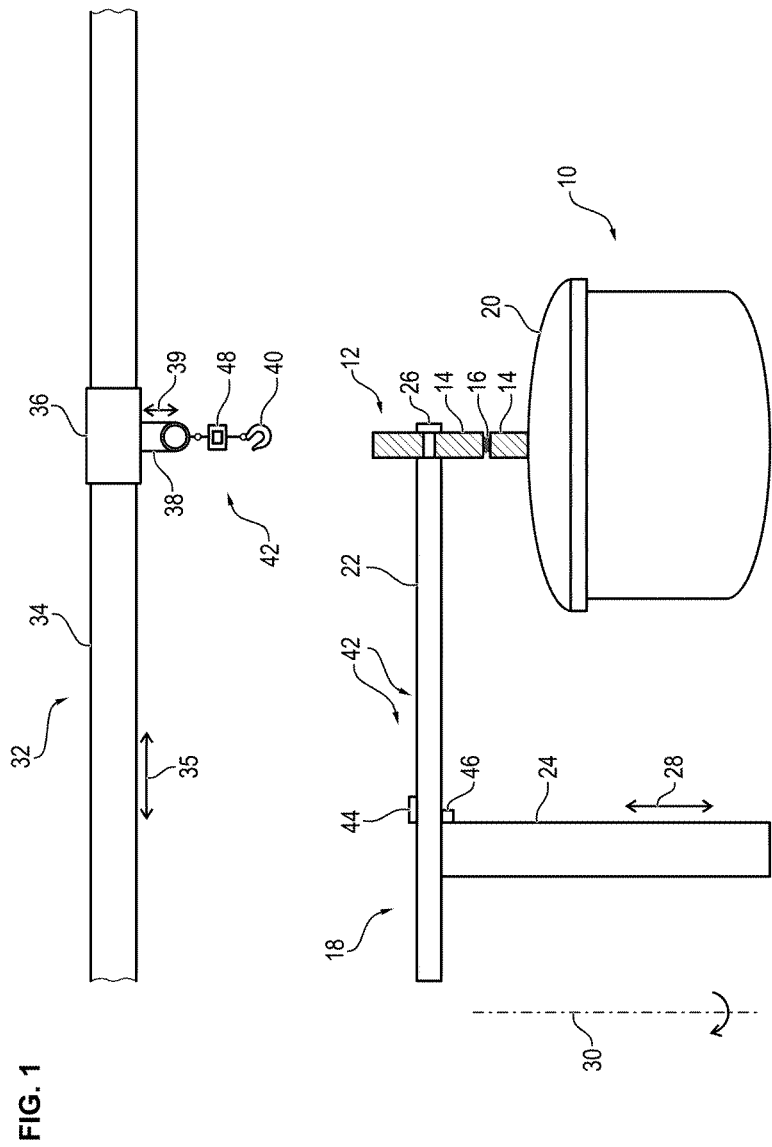
FIG. 1 is an illustration of a system containing an electric furnace and a device for determining a consumption of electrode material of the electric furnace according to a first embodiment of the invention.

Referring now to the figures of the drawings in detail and first, particularly to FIG. 1 thereof, there is shown a system containing an electric arc furnace 10, which receives for example steel scrap and optionally further additives as an input material, which is melted down in the arc furnace 10 by the thermal energy of arcs struck in the arc furnace 10.

In order to strike the arcs, the system has a bottom electrode (not shown in FIG. 1) which is arranged in the arc furnace 10 and is in direct electrical contact with the input material of the arc furnace 10, as well as an electrode column 12, which is composed of a plurality of elongate graphite electrodes 14, which are screwed together via threaded nipples 16 at their respective longitudinal ends. In practice, a plurality, in particular three, electrode columns 12 arranged parallel to one another can be used, in particular dispensing with the bottom electrode, only one electrode column 12 being shown in FIG. 1 for better clarity.

Furthermore, the system contains a holding device 18, on which the electrode column 12 is hung and starting from which the electrode column 12 extends from above into the arc furnace 10 in a substantially vertical direction through a hole in the furnace lid 20. The holding device 18 contains a substantially horizontal support arm 22, which is supported by a substantially vertical pillar 24. On its end on the furnace side, a support arm 22 has a clamp 26, in which the electrode column 12 is received and which can, for example, contain one or more clamping jaws by which the electrode column 12 is fixed in the clamp 26 or can be released from the clamp 26.

The electrode column 12 is held by the holding device 18 in a position in which the tip, arranged inside the arc furnace 10, of the electrode column 12 is located above the input material of the arc furnace 10 at a defined distance from the input material. By applying an electric voltage between the bottom electrode and the electrode column 12, arcs can be struck between the electrode column 12 and the input material of the arc furnace 10 and the input material can be melted due to the thermal energy released by the arc. The electrode column 12 is energized via the support arm 22, which is produced from an electrically conductive material for this purpose and is connected to a power source via cables (not shown in FIG. 1).

In order to be able to adjust the height of the electrode column 12, and in particular to facilitate feeding of the electrode column 12 necessary as a result of the burn-off of the electrode 12 during the melt operation of the arc furnace 10, the holding device 18 is height-adjustable, i.e. movable in the direction of the arrow 28. Furthermore, the holding device 18 can be raised together with the electrode column 12 and preferably together with the furnace lid 20 relative to the arc furnace 10 and is pivotable about a vertical axis 30 in order to be able to open the arc furnace 10, for example after it has been tapped, and in order to be able to charge the arc furnace 10 with new input material through the opening of the arc furnace 10 assigned to the furnace lid 20.

Furthermore, the system contains a transport device 32, which is constructed as a crane device with a substantially horizontal crane track 34, a crane carriage 36 movable along the crane track 34 in the direction of arrow 35 and a crane hook 40, which is hung on the crane carriage 36 by a cable 38 and can be raised and lowered in a vertical direction relative to the crane carriage 36 along the arrow 39. The positions and paths of movement of the transport device 32 and the holding device 18 are aligned such that the crane carriage 36 is movable into a position vertically above the position of the clamp 26 of the holding device 18 in which the electrode column 12 received in the clamp 26 is hung on the transport device 32 or can be removed from it. For this purpose, the electrode column 12 can have a loop (not shown specifically in FIG. 1) or the transport device 32 can have a suitable coupling apparatus for hanging the electrode column 12 on it. New electrodes 14 can be transported by the transport device 32 to the electrode column 12 and connected thereto and the electrode column 12 can be removed from the holding device 18 if necessary or fed to the holding device 18.

Furthermore, the system contains a weighing device 42, which in the present embodiment contains a strain gauge 44 attached to the upper side of the support arm 22, which measures a strain caused in the support arm 22 by the weight of the electrode column 12, as well as a load cell 46, which is attached in the region of the connection between the support arm 22 and the pillar 24 and is connected to the support arm 22 and the pillar 24 such that it can perform measurements effectively and crane scales 48 hung on the crane carriage 36 of the transport device 32 and arranged between the crane carriage 36 and the crane hook 40.

The strain gauge 44 and the load cell 46 each serve to measure the weight of the electrode column 12 while it is held by the holding device 18, for example between two consecutive melt operation intervals of the arc furnace 10. Whereas the crane scales 48 serve to measure the weight of the electrode column 12 while it is hanging from the transport device 32, for example while the electrode column 12 is being lowered relative to the arc furnace 10 and the holding device 18 by the transport device 32, for example after a new electrode 14 has been fixed to the electrode column 12 by the nipple.

The determination of the weight of the electrode column 12 carried out by the weighing device 42 facilitates the precise determination of the consumption of electrode material of the arc furnace 10, the determination of consumption being integrated in the operation of the arc furnace 10 such that it can be carried out at minimal additional cost. In practice, the weighing device 42 can, of course, also contain just two or one of the various components strain gauge 44, load cell 46 and crane scales 48 illustrated in FIG. 1.

Figure 2:
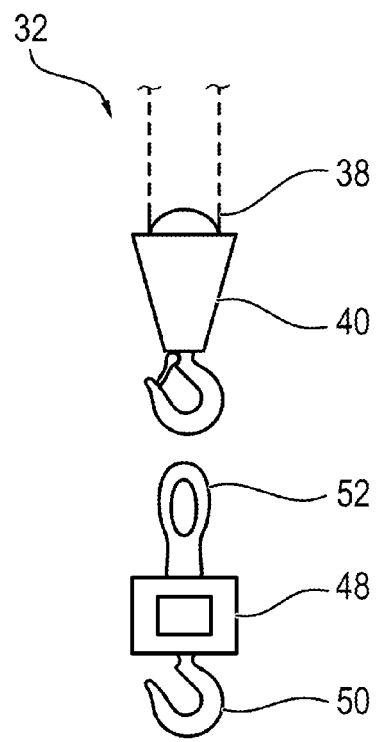
FIG. 2 is an illustration of a device for determining the consumption of electrode material of the electric furnace according to a second embodiment of the invention.
Figure 2:
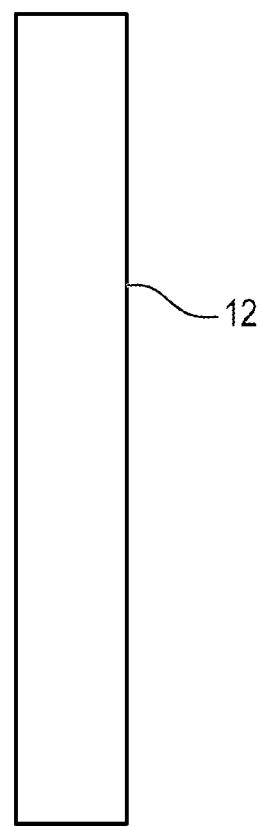

FIG. 2 shows a detailed view of a device for determining the consumption of electrode material of the electric furnace according to a second embodiment, which device contains the crane scales 48, which have a hook 50 on one end for coupling with the electrode column 12 and which have an eye 52 on their other end for hanging the crane scales 48 on a crane hook 40 of a transport device 32, which is configured as shown in FIG. 1.

The following is a summary list of reference numerals and the corresponding structure used in the above description of the invention:
10 Electric furnace/arc furnace
12 Electrode column
14 (Graphite) electrode
16 Threaded nipple
18 Holding device
20 Furnace lid
22 Support arm
24 Pillar
26 Clamp
28 Arrow
30 Vertical axis
32 Transport device
34 Crane track
35 Arrow
36 Crane carriage
38 Cable
39 Arrow
40 Crane hook
42 Weighing device
44 Strain gauge
46 Load cell
48 Crane scales
50 Hook
52 Eye

The invention claimed is:

1. A method for determining consumption of electrode material during a production of steel in an electric arc furnace, the method comprises the step of:
determining a weight of at least one electrode column disposed inside the electric arc furnace or to be introduced into the electric arc furnace, without removing the electrode column from the electric arc furnace, by using at least one weighing device carrying out a continuous or quasi-continuous determination of the weight of the electrode column with a temporal resolution of from 1 to 500 Hz without having to modify an operating procedure of the electric furnace and without additional electrode column movements having to be carried out.

2. The method according to claim 1, which further comprises automatically determining the weight of the at least one electrode column.

3. The method according to claim 1, which further comprises determining the weight of the at least one electrode column at at least two different points in time.

4. The method according to claim 3, which further comprises determining the weight of the at least one electrode column before and after a melt operation interval of the electric furnace.

5. The method according to claim 1, which further comprises:
integrating the weighing device in an operating device of a system containing the electric furnace, and integrating the weighing device in a transport device with which the electrode column disposed inside the electric furnace and held in the electric furnace by a holding device, is received and transported in the electric furnace and/or transported out of the electric furnace, and/or with which the electrode column disposed outside of the electric furnace is transported into the electric furnace, and/or the weighing device is integrated in the holding device by which the electrode column is held in position during the operation of the electric furnace, in an adjusting device of the holding device, with which the holding device is adjustable, including being height-adjustable.

6. The method according to claim 1, which further comprises determining the weight of the at least one electrode column using at least one strain gauge, at least one force transducer and/or at least one pressure measuring element disposed in a hydraulic system for adjusting a holding device for the electrode column.

7. The method according to claim 1, which further comprises providing an arc furnace as the electric furnace.

8. The method according to claim 6, which further comprises selecting the strain gauge from the group consisting of a metallic strain gauge and an optical strain gauge.

9. A device for determining consumption of electrode material during a production of steel in an electric arc furnace, the device comprising:

at least one weighing device for a continuous or quasi-continuous determination of a weight of at least one electrode column disposed in the electric arc furnace during a production of steel in the electric arc furnace without having to modify an operating procedure of the electric arc furnace and without additional electrode column movements having to be carried out, said weighing device being integrated in a transport device for transporting and holding the electrode column.

10. The device according to claim 9, wherein said weighing device determines the weight of the electrode column automatically.

11. The device according to claim 9, wherein said transport device is configured to receive the electrode column that is disposed inside the electric furnace and held in the electric furnace by a holding device and to transport the electrode column inside the electric furnace and/or transport the electrode column out of the electric furnace and/or to transport the electrode column disposed outside of the electric furnace into the electric furnace.

12. The device according to claim 9, wherein said weighing device is integrated in a holding device which is configured to hold the electrode column during a melt operation of the electric furnace.

13. The device according to claim 12, wherein said weighing device is integrated in a support arm of the holding device.

14. The device according to claim 12, wherein said weighing device has at least one of a strain gauge, at least one force transducer or at least one pressure measuring element disposed in a hydraulic system for adjusting the holding device for the electrode column.

15. The device according to claim 14, wherein said strain gauge is selected from the group consisting of a metallic strain gauge and an optical strain gauge.

16. The device according to claim 9, wherein said weighing device is configured such that said weighting device determines the weight of the at least one electrode column continuously or at least quasi-continuously with a temporal resolution of from 1 to 500 Hz.

17. The device according to claim 9, wherein the electric furnace is an arc furnace for producing steel.

* * * * *